United States Patent [19]

Grundy

[11] Patent Number: 4,743,749
[45] Date of Patent: May 10, 1988

[54] SELF COMPENSATING CIRCUIT FOR MEASURING RAPIDLY OCCURRING OPTOELECTRONICALLY DETECTABLE EVENTS

[75] Inventor: Reed H. Grundy, Murrysville, Pa.

[73] Assignee: PPG Industries, Inc., Pittsburgh, Pa.

[21] Appl. No.: 899,568

[22] Filed: Aug. 25, 1986

Related U.S. Application Data

[63] Continuation-in-part of Ser. No. 772,977, Sep. 5, 1985, Pat. No. 4,610,707.

[51] Int. Cl.$^4$ .................................................. G01J 1/32
[52] U.S. Cl. ...................................... 250/205; 250/561; 250/214 AG
[58] Field of Search ............... 250/205, 206, 208, 209, 250/214 AG, 561, 562; 356/429, 430

[56] References Cited

U.S. PATENT DOCUMENTS

| | | | |
|---|---|---|---|
| 2,295,795 | 9/1942 | Keeler | 73/160 |
| 2,565,500 | 8/1951 | Ingham, Jr. | 250/562 |
| 3,303,698 | 2/1967 | Loepfe | 250/562 |
| 3,729,635 | 4/1973 | Shottenfeld et al. | 250/562 |
| 4,007,457 | 2/1977 | Aeppli | 356/430 |
| 4,056,536 | 9/1977 | Smithgall, Sr. | 540/586 |
| 4,060,965 | 12/1977 | Schwartz | 57/265 |
| 4,097,731 | 6/1978 | Krause et al. | 250/214 AG |
| 4,184,769 | 1/1980 | Aeppli | 356/430 |
| 4,203,032 | 5/1980 | Haunstetter et al. | 250/205 |
| 4,281,325 | 7/1981 | Jarva | 250/205 |
| 4,352,013 | 9/1982 | Fasig et al. | 250/205 |
| 4,577,096 | 3/1986 | Beery et al. | 250/205 |

Primary Examiner—David C. Nelms
Assistant Examiner—William L. Oen
Attorney, Agent, or Firm—John E. Curley

[57] ABSTRACT

A circuit is described which can be used to record rapidly occurring faults in a slowly reacting circuit which is self compensating so that the photoelectric light emitters used in the circuit have their flux maintained constant.

2 Claims, 4 Drawing Sheets

SELF COMPENSATING CIRCUIT FOR MEASURING RAPIDLY OCCURRING OPTOELECTRONICALLY DETECTABLE EVENTS

This application is a continuation-in-part U.S. application Ser. No. 772,977, filed Sept. 5, 1985, now U.S. Pat. No. 4,610,707.

BACKGROUND OF THE INVENTION

The present invention relates in general to a control circuit for testing equipment which is simple in construction, reliable in service and inexpensive to manufacture compared to devices currently available for performing similar functions. The circuit can be used in a device for detecting and counting broken filaments in a strand, for example. It may also be used, in a modified version, as a self compensating measuring circuit for use in a tachometer or any other similar device used to measure rotational or linear speeds, by measuring the presence or absence of light using apertured discs and/or strips.

In systems used heretofore to measure or detect random faults or to measure rotational or linear speeds utilizing light sources, the measuring devices typically have used two circuits, one circuit to sense the light and one circuit to control the emission of the light. Thus, one circuit used to control the light emission required a control loop that was optically complicated since it required beam splitters, detectors and feedback amplifiers to provide a constant light flux. The other circuit of the prior art devices, where the light beam receiver was employed was subject to drifts due to temperature and therefore required automatic control circuits for temperature control and compensators within the circuit to eliminate such drifts.

In accordance with the instant invention, a system is provided which eliminates the need for such complicated circuitry rendering Applicant's system simple in construction, very reliable in service, and as heretofore stated, inexpensive from a manufacturing standpoint so that it can readily be used in devices such as tachometers and optical devices utilized to detect broken filaments in textile strands, to name but two applications.

SUMMARY OF THE INVENTION

In accordance with the instant invention, a novel circuit is provided which involves a light beam emitter, a light detector and means to produce a signal in response to the intensity of the detected light. Means are provided to amplify the signal from the detector and produce a second signal which is used to power the light beam emitter, regulate its flux and indicate interruptions.

In accordance with one embodiment of the instant invention, a self compensating circuit is provided with a light emitting source and a receiver. The light receiver is connected to a voltage divider resistor circuit carrying on one end a variable bias resistor for feeding signals into an operational amplifier. Connected across the amplifier is a feedback resistor and the output of the amplifier is connected to a second amplifier which has a capacitor coupled in parallel thereto. The output of the second amplifier is connected to a driver amplifier which in turn, introduces power to the light source of the self compensating circuit.

In another embodiment of the invention, a mirror image circuit of the self compensating circuit is provided which involves a second light source and a second detector with all other elements being the same as the single light source system so that in utilizing the second circuitry on an apertured disc of a tachometer system, for example, one circuit will be detecting light through the apertures in the disc while the other circuit will be in a non-detecting stance or mode when the light is being interrupted by a plate positioned between the apertures.

It is therefore an object of the invention to provide a novel circuit for sensing or testing equipment which is simple in construction.

It is a further object of the invention to provide an self compensating circuit for sensing and testing equipment which is not subject to drifts normally associated with such devices.

It is a further object of the invention to provide a circuit for sensing and testing equipment that permits the same circuit to be utilized for sensing and emitting a light beam and eliminating the necessity for utilizing a separate circuit for each function.

These and other objects of the invention will become obvious from the ensuing description.

BRIEF DESCRIPTION OF THE DRAWINGS

The invention will become more apparent to those skilled in the art from a consideration of the following detailed description of the preferred embodiments of the invention taken in conjunction with the accompanying drawings in which.

DETAILED DESCRIPTION OF THE PREFERRED EMBODIMENTS

Figure 1:
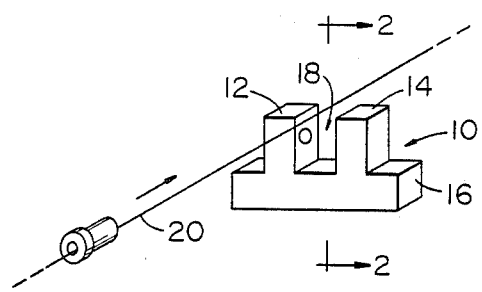
FIG. 1 is a perspective view of an optoelectronic module arranged for detection of broken filaments in a textile strand.
Figure 2:
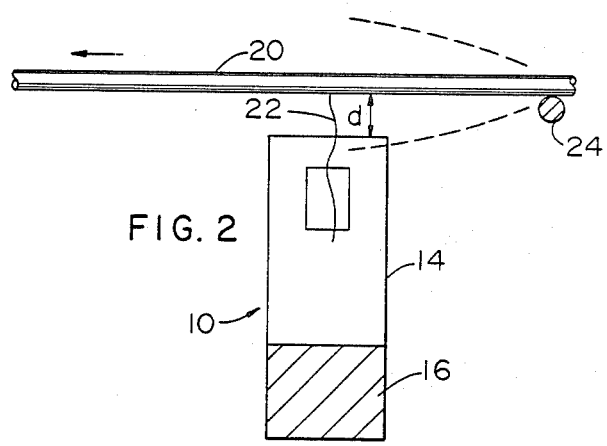
FIG. 2 is an enlarged cross-sectional view of the module taken along lines 2—2 of FIG. 1.

Turning now to a more detailed consideration of the self compensating circuits of the the present invention, there is illustrated in FIG. 1 the use of one embodiment of such a circuit used in an optoelectronic measuring system for detecting random faults in a moving article such as a glass fiber strand. The system shown in FIG. 1 contains an optoelectronic module 10, which is a commercially available optical detector. The module 10 includes a pair of upstanding legs 12 and 14 supported on a base 16, and spaced apart to define a measuring channel 18. A suitable light source such as a light-emitting diode (LED) (not shown) is mounted in one of the upstanding legs; for example, leg 12, while a suitable light detector, such as a phototransistor (not shown), is mounted in the other leg; for example, leg 14. The LED and the light detector define a light path across channel 18, and circuit means (to be described) is provided to respond to the output of the light detector and to produce an output pulse whenever the light beam is interrupted. A strand or length of yarn 20, which is to be monitored for the presence of broken fibers, is so located as to pass over the detector channel 18 of the module 10. As illustrated in FIG. 2, the path of the strand is preferably flush with the top of the module 10, but centered over the channel 18, so that the strand itself does not interrupt the light beam, but so that any broken filaments extending from the strand, such as the filament 22 illustrated in FIG. 2, will pass through the beam for detection. As previously explained, strand 20 is made up of a large number of filaments twisted together to form a unitary strand having the desired thickness and strength characteristics. In the manufacture of such strand, which may involve twisting together of numerous filaments, or during the winding and rewinding operations which occur in the transfer of the strand to a bobbin and then to a warp bar, for example, some of the filaments may break. Such breakage may be due to excessive mechanical stresses during the winding or twisting operations, or may be due to faulty filament structure caused by a problem in the manufacturing process. In either case, the existence of such broken filaments degrades the quality of the strand, so it is extremely desirable to detect them, and to determine the effect they they have on the overall quality of the material, by determining the number of broken filaments per unit length of the strand to a high degree of accuracy and reliability. Since the number of broken filaments per unit length may be an indication of the quality of the strands the photodetected broken filaments themselves may reflect change or errors in manufacturing parameters, so the accurate detection of such filaments is an important factor in process control.

Since broken filament ends tend to extend out of the strand at approximately right angles to the axis of the strand when they break, it has been found that the strand does not have to pass through the detector channel 18, but, instead, can be located outside the detector module, as shown in FIG. 2. In tests, it has been found that the distance between the top of the detector 10 and the strand 20 should be between zero and one millimeter. The strand preferably is supported by a smooth guide rod 24 located upstream from the detector to prevent transverse motion of the strand due to vibrations and the like from carrying the strand itself into the path of the light beam. Because the guide rod tends to collect pieces of broken filament which could reach into the channel 18 and affect the output of the light detector, it is preferred that the guide rod be at least 2.5 cm away from the detector module.

It will be understood that the broken filament ends 22 may extend in any direction radially outwardly from the strand 20, so that not all of the broken filaments will pass through the light beam for detection. However, the detector will sense a large proportion of the filament, and since over a long length of the strand the broken ends will tend to be uniformly distributed around the circumference of the strand, although randomly distributed along its length, the reading obtained by the module 10 will be directly proportional to the total number of broken filament ends. Accordingly, an accurate count for purposes of determining the quality of the strand, and for determining the effect on breakage or changes in the manufacturing process or in the handling of the strand, will be provided by the present invention.

Figure 3:
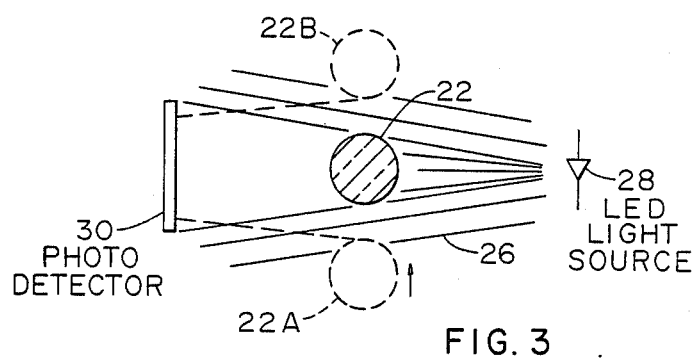
FIG. 3 is a diagrammatic illustration of the light interruption pattern in the module of FIG. 1.
Figure 4:
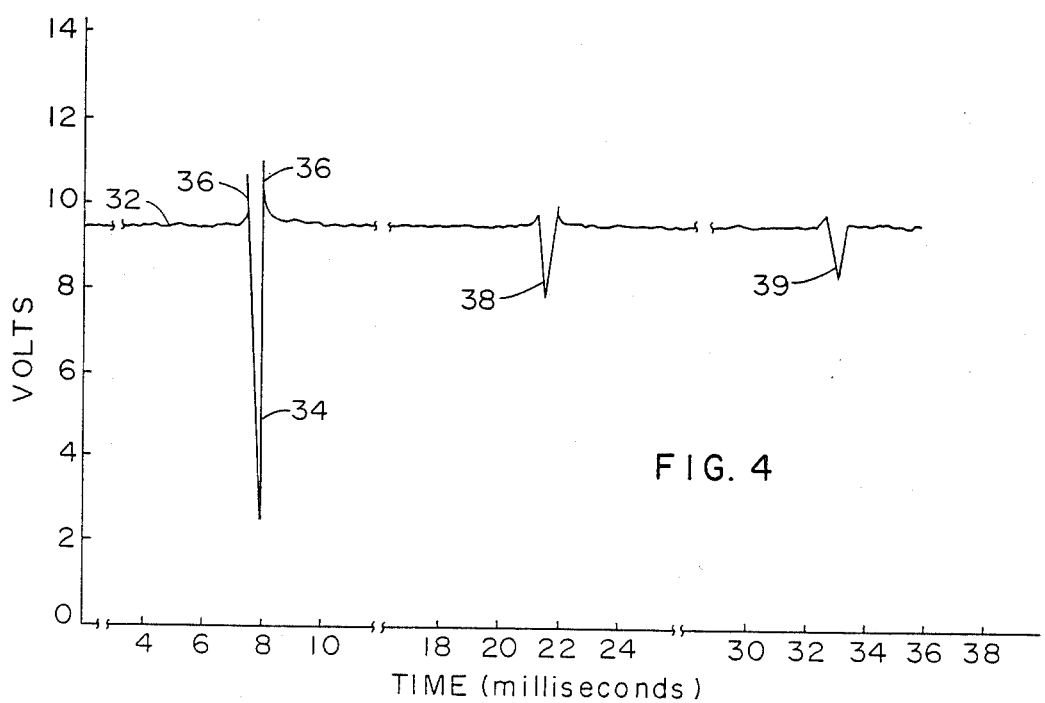
FIG. 4 is a diagrammatic trace showing the output from the module of FIG. 1 for various diameters of broken filaments.

The module 10 is a very high-speed device, and is capable of measuring filaments which pass through the light path at a high rate. As shown in FIG. 3, the filament end 22 interrupts the light beam 26 in the path between the light source 28 and a detector 30. The passage of the filament 22 through the light beam produces at the detector output a pulse 32, illustrated in FIG. 4, the width of the pulse being dependent on the speed of the filament and its amplitude being dependent on the diameter of the filament FIG. 4 is a diagrammatic illustration of an oscilloscope trace of the output from detector 30. The detector normally produces an output 32 at a level determined by the intensity of source 28, with the pulse 34 being produced by a filament 0.0016 inch in diameter passing through the light beam 26. It will be noted that small positive peaks 36 occur before and after the negative going pulse 34, which peaks are caused by light reflection from the surface of the filament at positions 22A and 22B as the filament approaches the light beam 26 and as it leaves it.

FIG. 4 also illustrates at 38 and 39 the pulses produced by smaller diameter filaments, pulse 38 being produced by a filament 0.0003325 inch in diameter, the pulse 39 being produced by a filament 0.000275 inch in diameter. It will be understood that reduced amplitude pulses could also be produced by filament ends that do not extend all the way through the light beam in the vertical direction.

Figure 5:
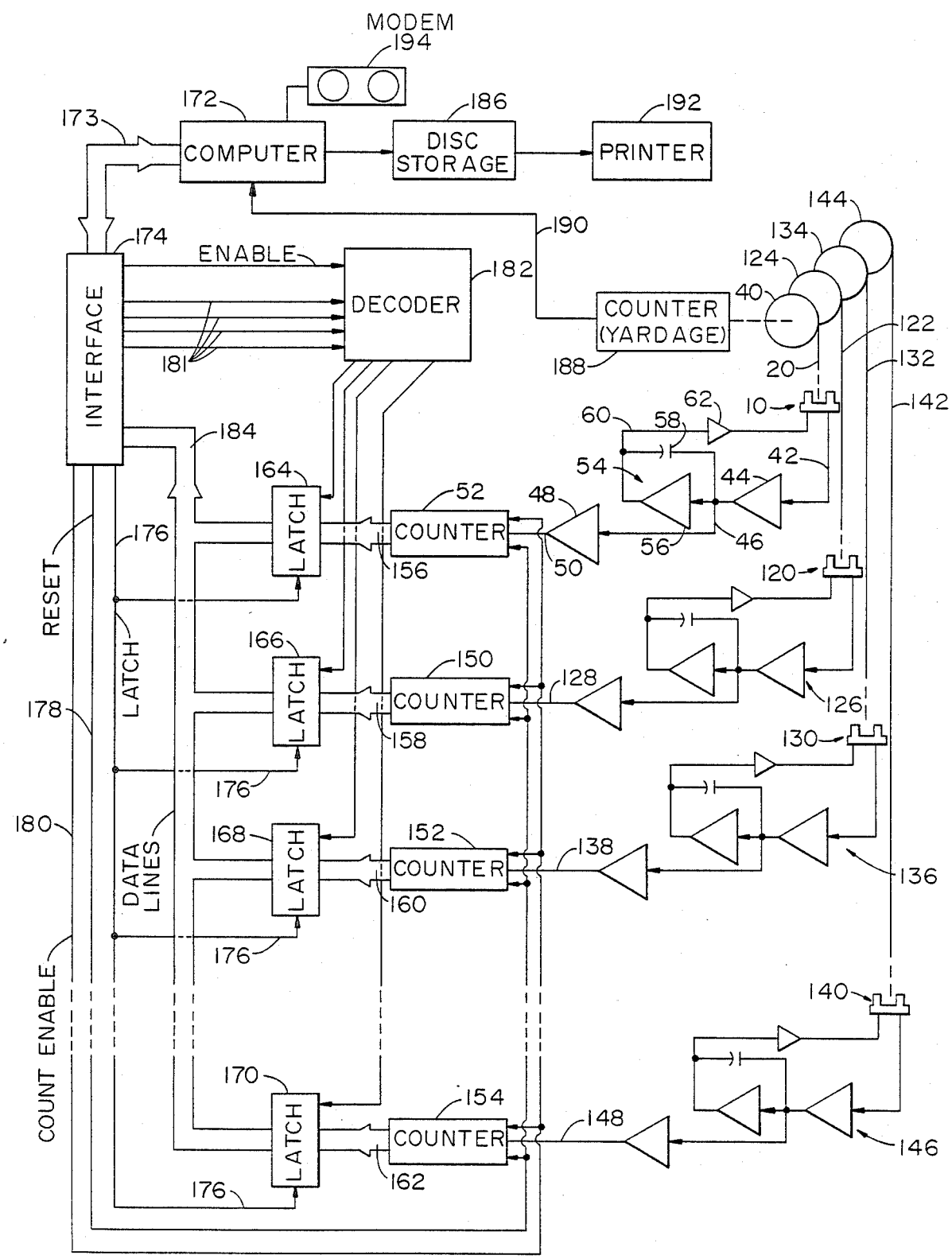
FIG. 5 is a block diagram of the circuitry for a system using the present invention.

The circuit and system for responding to the pulses produced by filaments passing through the light beam 26 is illustrated in FIG. 5, to which reference is now made. The optoelectronic module 10 is associated with filamentary strand 20 which may be supplied from a suitable bobbin 40. The strand passes by the module in the manner described above, and the photosensitive detector 30 carried by the module produces an output signal on line 42. This signal is fed through an operational amplifier 44, the output of which is a series of pulses, such as the pulse train 32 illustrated in FIG. 4. These pulses, which indicate the presence of broken filaments, are supplied by way of line 46 to a threshold detector 48 which is set to a predetermined level so that only pulses which exceed that level will produce an event pulse on detector output line 50. Thus, the threshold detector 48 serves to eliminate noise and the like which might provide a false reading of the number of broken filaments. The event pulse on output line 50 is supplied to a suitable counter 52 which then counts the number of filament ends detected by module 10.

It has been found that over a period of time the intensity of the light beam 26 may decline; accordingly, a feedback loop is provided to compensate for that decline. One of the reasons for the decline is the fact that the strand 20 normally is coated with a protective binder material. During the processing of the strand, some of the binder material may be scraped off, as by the support 24, and such material can collect on the optics of the module 10, reducing the intensity of the light beam. The feedback loop to compensate for this consists of an integrator circuit generally indicated at 54 and including an amplifier 56 and a parallel capacitor 58. The output of the integrator circuit is supplied by way of line 60 to a driver amplifier 62 which in turn supplies power to light source in the detector. As the intensity of the light beam declines, the output of the drive 62 is increased by the integrator circuit 54 to produce a higher output from the light source, thereby restoring the light beam to its preset intensity. A low pass filter circuit could be used in the feedback loop in lieu of the integrator circuit but is not preferred.

Figure 6:
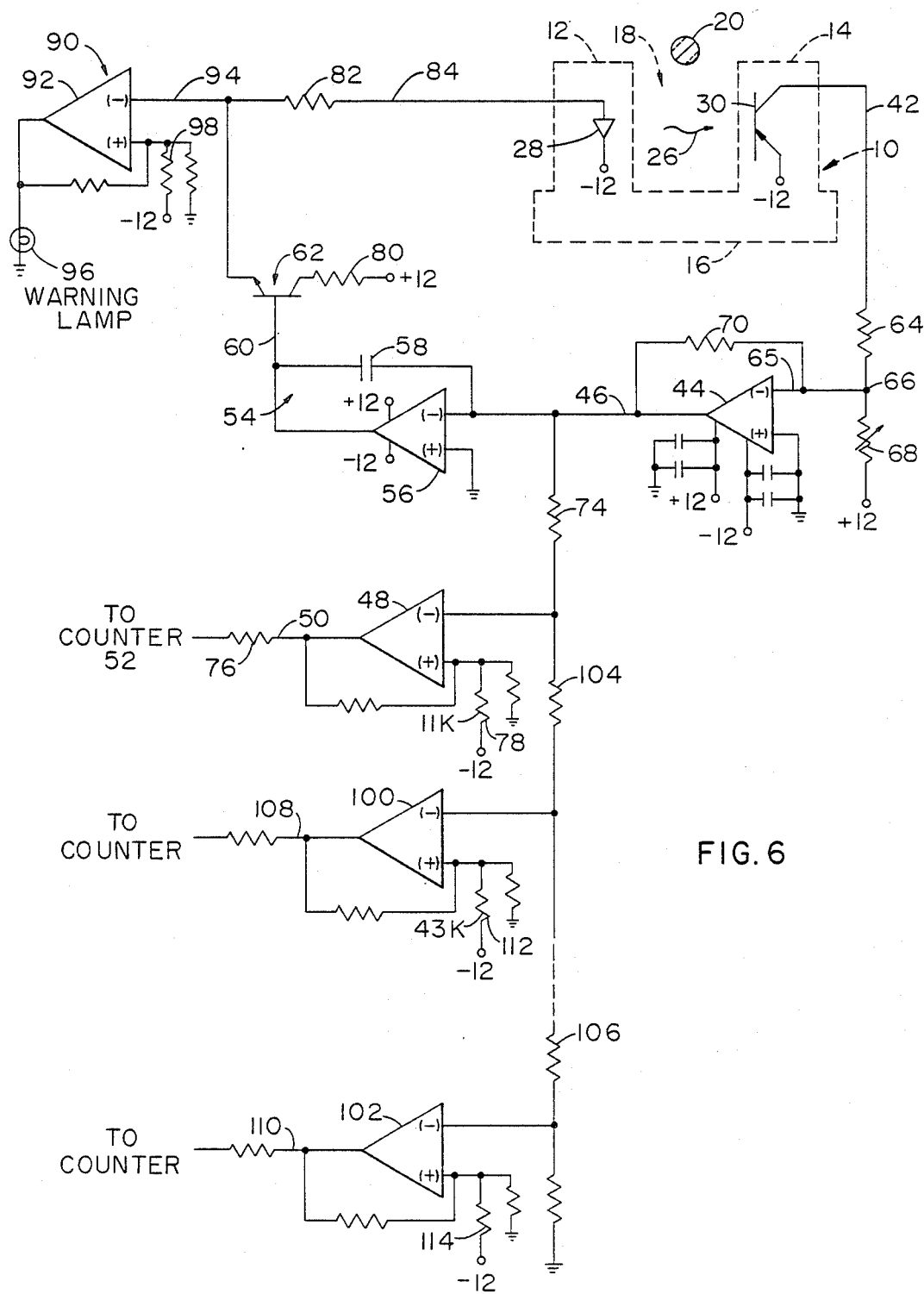
FIG. 6 is a schematic diagram in partial block form showing one embodiment of the self compensating circuit of the instant invention.

The filament detector circuitry shown in block diagram form in FIG. 5 is illustrated in more detail in FIG. 6, where one embodiment of the self compensating circuit of the invention is shown to involve a light source 28 shown as an light emitting diode (LED) mounted within the leg 12 of module 10 to produce a light beam 26 across the detector channel 18. The light beam strikes a light detector such as a phototransistor 30, which includes a grounded emitter and a collector connected to the output line 42. Line 42 includes a voltage divider resistor 64 and is connected, in this illustration, to the negative input 65 of operational amplifier 44. Also connected to this input, by way of junction 66, is a variable bias resistor 68 by means of which the normal output of the amplifier 44 is established in the absence of a filament end. This normal output level is illustrated in FIG. 4 at 32, as explained above. A feedback resistor 70 is connected from the output 46 of amplifier 44 to the input 65.

Output line 46 is connected through limiting resistor 74 to the negative input of a threshold detector 48, the output of which is connected by way of line 50 and resistor 76 to the counter 52. The positive input of threshold detector 48 is connected through bias resistor 78 to a source of negative bias voltage, the size of the resistor 78 determining the threshold at which the detector becomes conductive to produce an output pulse on line 50.

The signal on line 46 from the operational amplifier 44 is also supplied to the integrator network 54, which includes the operational amplifier 56 and the capacitor 58. The output of the integrating circuit 54 is applied by way of line 60 to the base of a driver transistor 62, the collector of which is connected through resistor 80 to a source of bias voltage and the emitter of which is connected through a resistor 82 and line 84 to the LED 28 to supply the drive current for the LED device. A portion of the current output from detector 30 thus is fed back through operational amplifier 44 and the integrator circuit 54 to regulate the conductivity of drive transistor 62, the integrating network 54 serving to smooth out the effects of the pulses 32 produced by the passage of broken filaments through the light beam and to stabilize the drive current to the LED.

Resistor 68 provides a bias current to node 66 which, by the feedback nature of the circuit, is exactly balanced by the current produced by photo detector 30. Momentary interruptions or slight decreases in the amount of light flux 26 cause a slight unbalance or decrease in the current at node 66 which is compensated for by the output of amplifier 44 changing its output voltage so that the current through feed back resistor 70 exactly compensates for the momentary decrease in the current entering node 66. It can be appreciated that the voltage on conductor 46 will therefore be an indication of the commencement of a diminishing of the light flux 26. This signal is then amplified to indicate passage of small defects such as broken filaments through the light flux 26.

As the normal current 32 (FIG. 4) from the detector gradually decreases in degree, for example, because of aging of the LED or because of an accumulation of dust, binder material, or the like on the optics of the module 10, the bias applied to amplifier 44 through variable resistor 68 will change the amplifier output appearing on the line 46. This change then varies the output produced by the integrator network 54 to increase the current flow through driver transistor 62, thus restoring the output of the LED to its preset intensity level. In this way, the integrator circuit 54 and the driver transistor 62 keep the intensity of beam 26 constant in the absence of a filament. If desired, a level detector 90, including an operational amplifier 92 connected by way of line 94 to the input to the LED may be provided to sense the current being supplied to the LED. The output of amplifier 92 may be connected to a warning lamp 96 to provide an indication when the current level to the LED exceeds a predetermined value, set by the bias resistors 98 connected to a second input to amplifier 92.

The circuit of FIG. 6 as thus far described provides an output signal on line 50 each time an event pulse 34 (see FIG. 4) occurs which exceeds a predetermined amplitude, and provides a count of filament ends where the filaments exceed a preselected diameter. If desired, a plurality of similar threshold circuits may be provided, as indicated by the threshold circuits 100 and 102. These circuits receive their inputs from line 46 through respective voltage divider resistors 104 and 106, and produce outputs on their corresponding output lines 108 and 110. The pulse amplitude to which each threshold detector responds is determined by the bias resistors 112 and 114, respectively. By proper adjustment of the bias resistors 78, 112 and 114 for the threshold detectors 48, 100, and 102, these circuits can produce output pulses to respective counters to produce event pulses corresponding to selected filament sizes so that a measure of the distribution of filament diameters measured by a single detector 10 can be obtained.

FIG. 6 illustrates the circuitry for a single optoelectronic module 10 which measures the presence of broken filaments in a single strand 20. Module 10 and its circuitry constitute a single detector unit. As illustrated in FIG. 5, a plurality of such units may be provided, each measuring a different strand being supplied from a different bobbin. Thus, for example, the module 10 provides a measure of strand 20, a second optoelectronic module 120 with its associated circuitry may be arranged to measure a second strand 122 supplied from a bobbin 124, a third optoelectronic module 130 may be provided to measure a third strand 132 supplied by a third bobbin 134, and so on, with a module 140, representing a fourth optoelectronic module, measuring a corresponding strand 142 supplied by a bobbin 144. Each of the modules 120, 130 and 140 is connected to a corresponding detector circuit generally indicated at 126, 136 and 146, respectively, each of which is similar to that illustrated in FIG. 6, and each of which produces a train of output event pulses on its corresponding output line 128, 138 and 148, respectively. The train of event pulses on each of these output lines represents the number of broken filaments on the corresponding strands 122, 132 and 142.

As previously stated, the train of output pulses on line 50 is supplied to a corresponding counter 52. In similar manner, the outputs on lines 128, 138 and 148 are connected to corresponding counters 150, 152 and 154, respectively, to provide continuous counts of the random event pulses being provided by their respective detector units.

Although the output lines 50, 128, 138, and 148 are shown as being directly connected to their corresponding counters 52, 150, 152, and 154, it may be desirable, in some instances, to incorporate suitable buffer amplifiers (not shown) in those lines to shape the pulses before they are supplied to the respective counters.

The data in each of the counters is supplied by way of data lines 156, 158, 160, 162, respectively, to corresponding latch circuits 164, 166, 168, and 170. Under the control of a suitable computer 172, which may be a Hewlett-Packard Module HP216, for example, and through data line 173 and an interface network 174, the latching circuits are periodically activated to latch the event count data then in the respective counters. The latching signal is provided by way of line 176 to each of the latch networks. The latching signal is followed by a reset signal on line 178 which is applied to each of the counters 52, 150, 152, and 154, to reset them to zero after the counter content has been latched. Thereafter, a count enable signal is provided by the control computer on line 180 to restart each of the counters.

After the data in the counters has been latched, the computer 172, by way of interface 174 and data lines 181, activates a decoder 182 which operates to sequentially select each of the latches, in turn, to transfer the data contained therein by way of data lines 184 through the interface 174 and data lines 173 to computer 172. The data so obtained from the counters is stored at the computer, for example, in a suitable disk storage 186 together with data concerning the length of the strand supplied to the individual detector units. Strand length data may be obtained by way of strand length counter 188, by bobbin weight, or by any other conventional manner. This data is supplied to the computer 172 by way of line 190 and enables the computer to determine, among other things, the latching period of the data, and, ultimately, the number of broken filaments counted per unit length of the strand being monitored or the number of yards between each broken filament detected. For example, counter 52 can be a 1 bit (flip flop) binary counter and the computer cycle time can be made sufficiently small so as to eliminate the possibility of two broken filaments occurring within one cycle. Upon detection of a broken filament by a given counter, the accumulated yards in the yardage counter 188 is recorded and stored for the data associated with that counter. Subsequent events are similarly recorded by counter 188. If desired, the information obtained by the computer may be printed by a printer 192 or may be supplied by way of a modem 194 to a remote location for storage and further processing. The yardage counter 188 may be any conventional counter and may be sensitive either to the motion of the strand or the rotation of the drive capstan 34 on which the strand is moved. Individual counters may be provided for each strand, or one counter may be used to provide a single reading which may then be used for the calculations for all of the strands.

By utilizing a high-speed detector and high-speed digital circuitry, the system of the present invention is capable of obtaining an accurate count of the number of broken filaments over a relatively long Period of time, so that highly accurate measurements of the average number of breaks in a unit length of strand can be obtained. It has been found that, because of the random nature of filament breakage, in order to accurately and reliably detect a 10 percent difference in quality between strands, it is necessary to obtain a count of the number of broken filaments in 0.85 million yards of fiber glass strand. If it is desired to increase the resolution of the system so as to be able to detect a 5 percent difference in quality with a high degree of reliability, it is necessary to obtain measurements from 3.4 million yards of strand. In order to increase the resolution to detect a 1 percent difference in quality between two strands, it is necessary to measure 104.3 million yards of strand. Such measurements would not be practical with prior art systems, since they are far too slow to permit the measurement of the quantity of strand indicated. However, with the present invention, even very subtle changes in the manufacturing process of the fibers, such as would produce only a 1 percent change in the amount of filament breakage, can readily and accurately be detected, thereby allowing far superior control of the manufacture and processing of fiber glass strands.

Although the present invention has been described in terms of a broken strand detector, it will be apparent that it is equally useful in determining the quality of yarn formed from multiple strands. Furthermore, as explained with respect to FIG. 6, the system is also able to obtain for each strand being measured a distribution of the diameters of the broken filaments by providing additional threshold detectors with corresponding counters. The output of those additional counters would also be connected to corresponding latching networks, and connected to the computer for selection and storage in the manner described with respect to FIG. 5.

A further use of the present system is in the detection of and measurement of the amount of binder material which is shed by the strand as it passes by the detector. The threshold detector 90 which measures the change in the level of the drive current to the LED 28 and provides a warning signal when that current exceeds a predetermined value also provides a measure of the time period over which a predetermined change in intensity occurs, thereby providing a measure of the amount of binder being shed by the strand during that time.

It should also be noted that the detector units of the present invention may also be used to measure strand dimensions by moving the strand periodically into the detector channel and through the light beam 26. This motion of the strand itself will produce an output pulse, the amplitude of which can be used to determine the diameter of the strand. Furthermore, if desired, a pair of such detectors may be provided at right angles to each other for measuring the diameter of the strand in two directions, so as to determine strand flatness, or aspect ratio.

In order to obtain an accurate measure, the data in the counters 52, 150, 152, and 154 is latched at fixed increments. These increments can be determined by time; for example, once each minute, or may be determined by a predetermined length of the strand being measured; for example, every 500 yards. A preferred increment is the yardage count obtained from counter 188 so that accurate measurements are obtained even if the strands should stop in the middle of a count. In such a situation, the computer would simply wait until the strands restarted, and the proper yardage count was obtained, before latching the contents of the pulse counters 52, 150, 152, and 154, thereby ensuring accurate data.

Figure 7:
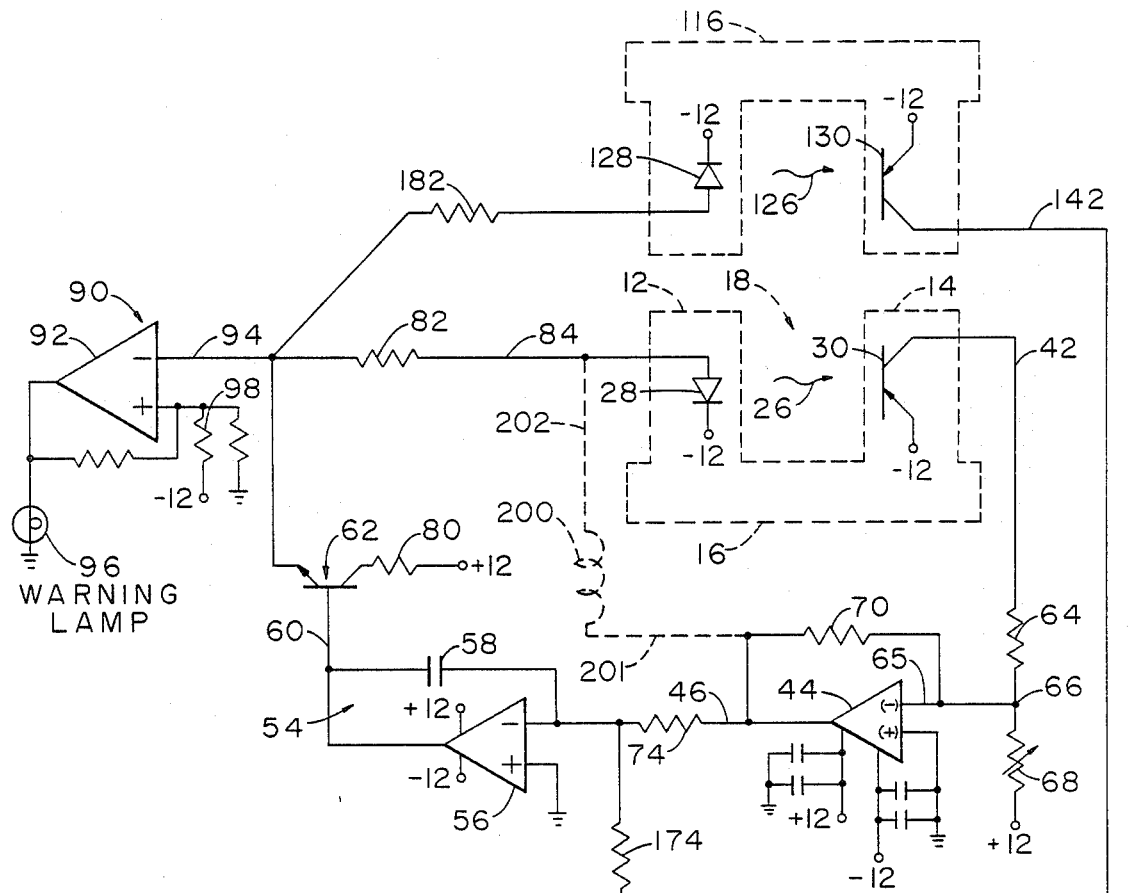
FIG. 7 is a circuit diagram of yet another embodiment of the self compensating circuit of the instant invention.

FIG. 7 is a schematic diagram of another embodiment of a circuit of the instant invention in which there is shown two light emitters 28 and 128. Each light beam emitter is controlled from the same driver amplifier 62.

Amplifier 62 is controlled by an amplifier 56 which in conjunction with capacitor 58 form an integrator 54. The input to the integrator 54 is controlled by the sum of the light levels from photo detectors, i.e., 30 and 130, the outputs of which are amplified by operational amplifiers 44 and 144.

The light paths 26 and 126 are positioned electrically 180° out of phase which insures that the sum of the light outputs of 30 and 130 are a constant. Therefore the outputs of amplifiers 44 and 144 when summed through resistors 74 and 174 produce a signal which is used by amplifier 56 to regulate the light flux constant in beam emitters 28 and 128.

Variable bias resistors 68 and 168 are used to adjust both the amount of flux and the balance between the two. If particulate matter should prevent some or all of light flux 26 or 126, from reaching detectors 30 and 130 respectively, the above described circuits will cause driver amplifier 62 to increase the current to light emitters 28 and 128. This current acting on resistors 82 and 182 will raise the voltage on conductor 94 to a voltage which is higher than that set by the circuitry 98 thus causing amplifier 92 to switch on lamp 96.

By virtue of the instant system, a circuit is provided in which the sensing element 30 is compared to a point via 68 by an amplifier 44 producing a signal in 46 that is proportional to any difference between the actual illumination and the set point. In order to remove steady state errors due to limited gain, amplifier 56 and capacitor 58 which form an integrator, the purpose of which is twofold, is provided. One is to reduce the error signal on 46 to zero by controlling the current in the light emitter 28 through transistor 62 the purpose of which is to supply current gain. Secondly, the elements 56 and 58 forming integrator 54 provide for a slow response, thereby rendering the circuit self compensating, while at the same time permitting rapid response to monitoring interruption of the light flux so that the light beam 28 cannot change in a rapid manner.

This permits sensing of momentary interruptibles of light flux 26 to be sensed at the output of 44 on line 46. It produces an output on 46 that is proportional to the percent of the area of phototransistor 30 that is obscured times the set point current fixed by resistor 68 times the feedback resistor 70. The integrator 54 can also be in the form of a low pass filter 200 connected by lines 201 and 202 to the light emitter 28. These elements are shown in dotted lines, since they are not the preferred embodiment but an alternative thereto. Alternatively, a low pass filter can be achieved by connecting a capacitor (not shown) between collector and base of transistor 62.

Figure 8:
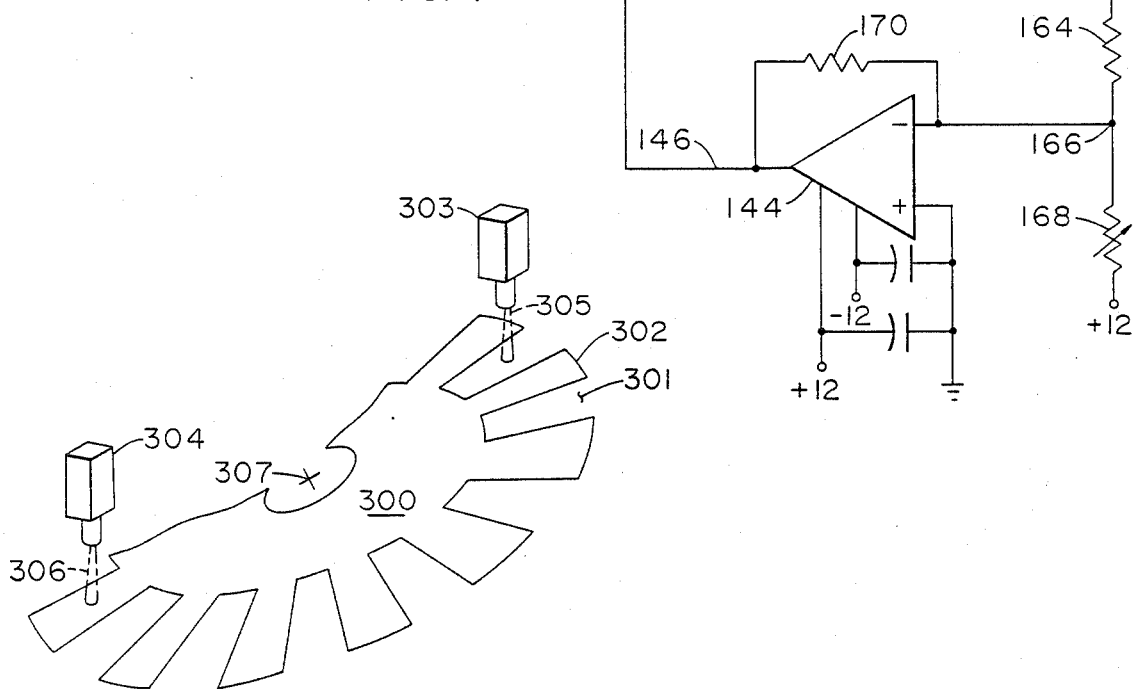
FIG. 8 is a diagrammatic illustration of a light source positioned above an apertured disc used for measuring rotational speed when coupled for example to a rotating shaft.

In FIG. 8 there is shown an optical disc 300 having apertures 301 and plates 302 thereon. Fixed at 180 electrical degrees from each other, as shown, are two light emitters 303 and 304 emitting beams 305 and 306. The disc 300 is placed on a rotatable plate which engages the walls surrounding center opening 307. The two light emitters, which have light detectors positioned on the opposite side of disc 300 in the path of beams 305 and 306 respectively, but not shown in the drawing, are activated. As the shaft rotates, the disc 300 rotates and the light beams 305 and 306 are alternately interrupted by the plate member 302. As will be understood by the skilled artisan, the amount of beam interruption by plates 302 on each of the beams when summed will always equal the constant set by the bias resistors 68 and 168.

While the present invention has been described with reference to certain descriptions and illustrated embodiments, obvious modifications may be made without departing from the spirit of the invention and the invention is not intended to be limited thereby except insofar as appears in the accompanying claims.

I claim:

1. A self compensating circuit comprising a first circuit having a light emitter and a light detector forming a first light path, means to produce a signal representing the intensity of the detected light, means to amplify said signal to produce a second signal, a second circuit having a second light emitter and a second light detector forming a second light path, means to produce a third signal representing the intensity and the detected light from said second light emitter, means to amplify said third signal to produce a fourth signal, said first and second light paths being electrically out of phase so that the sum of the second and fourth signal from the light outputs from the light detectors are a constant, means to feed the said second and fourth signals through a slowly reacting circuit means which produces a fifth signal, said fifth signal, when fed to said first and second circuits and their associated light emitters to thereby maintain the flux of each of said light emitters constant as the slow reacting circuits is subjected to rapid changes in each of the light fluxes of each light emitter caused by short interruptions of those light fluxes.

2. The self compensating circuit of claim 1 further including means for using said second and/or fourth signal as an indicator of a rapidly occurring change.

* * * * *